(12) United States Patent
Sengupta

(10) Patent No.: US 12,144,553 B2
(45) Date of Patent: Nov. 19, 2024

(54) DYNAMIC FLOW PHANTOM FOR IN VITRO CARDIAC INTERVENTION PRE-PROCEDURE PLANNING AND TESTING USING PATENT SPECIFIC 3D PRINTED ANATOMICAL MODELS

(71) Applicant: RUTGERS, THE STATE UNIVERSITY OF NEW JERSEY, New Brunswick, NJ (US)

(72) Inventor: Partho Sengupta, Morgantown, WV (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 1143 days.

(21) Appl. No.: 16/967,267

(22) PCT Filed: Mar. 5, 2019

(86) PCT No.: PCT/US2019/020748
§ 371 (c)(1),
(2) Date: Aug. 4, 2020

(87) PCT Pub. No.: WO2019/173336
PCT Pub. Date: Sep. 12, 2019

(65) Prior Publication Data
US 2021/0052328 A1    Feb. 25, 2021

Related U.S. Application Data

(60) Provisional application No. 62/640,272, filed on Mar. 8, 2018.

(51) Int. Cl.
*A61B 34/10*    (2016.01)
*B29C 64/393*    (2017.01)
(Continued)

(52) U.S. Cl.
CPC ............ *A61B 34/10* (2016.02); *B29C 64/393* (2017.08); *B33Y 50/02* (2014.12); *B33Y 80/00* (2014.12);
(Continued)

(58) Field of Classification Search
CPC . A61B 34/10; A61B 2034/105; B29C 64/393; B33Y 50/02; B33Y 80/00;
(Continued)

(56) References Cited

U.S. PATENT DOCUMENTS

2001/0019818 A1    9/2001   Yong
2010/0167251 A1    7/2010   Boutchko et al.
(Continued)

FOREIGN PATENT DOCUMENTS

WO    WO-2017165969 A1 *  10/2017

OTHER PUBLICATIONS

International Search Report in co-pending, related PCT Application No. 1920748, mailed May 24, 2019.

*Primary Examiner* — Jeffrey S Vanderveen
(74) *Attorney, Agent, or Firm* — Quarles & Brady LLP

(57) ABSTRACT

Disclosed are various embodiments for a dynamic flow apparatus for cardiovascular diagnosis and pre-procedure analysis of individual patients. The dynamic flow apparatus includes a three-dimensional (3D) cardiac model in an enclosed container. The 3D cardiac model can mimic an operation of an actual heart by pumping fluid through the 3D cardiac model and causing the model to expand and contrast. Data obtained from the operation of the 3D model can be used during a surgical procedure of an actual heart of an individual.

19 Claims, 3 Drawing Sheets

(51) Int. Cl.
  *B29K 29/00*    (2006.01)
  *B29L 31/40*    (2006.01)
  *B33Y 10/00*    (2015.01)
  *B33Y 50/02*    (2015.01)
  *B33Y 80/00*    (2015.01)
  *G09B 23/30*    (2006.01)
  *G09B 23/32*    (2006.01)

(52) U.S. Cl.
  CPC ............ *G09B 23/303* (2013.01); *G09B 23/32* (2013.01); *A61B 2034/105* (2016.02); *B29K 2029/04* (2013.01); *B29L 2031/40* (2013.01); *B33Y 10/00* (2014.12)

(58) Field of Classification Search
  CPC ...... B33Y 10/00; G09B 23/303; G09B 23/32; B29K 2029/04; B29L 2031/40
  See application file for complete search history.

(56) References Cited

U.S. PATENT DOCUMENTS

| | | | |
|---|---|---|---|
| 2012/0113108 A1* | 5/2012 | Dala-Krishna | G06T 7/12 345/419 |
| 2014/0069215 A1 | 3/2014 | Tavakoli et al. | |
| 2017/0103682 A1* | 4/2017 | Okayama | G06T 7/0012 |
| 2017/0116887 A1* | 4/2017 | Mchale | G09B 23/306 |

* cited by examiner

DYNAMIC FLOW PHANTOM FOR IN VITRO CARDIAC INTERVENTION PRE-PROCEDURE PLANNING AND TESTING USING PATENT SPECIFIC 3D PRINTED ANATOMICAL MODELS

CROSS-REFERENCE TO RELATED APPLICATIONS

This application is the 35 U.S.C. § 371 national stage application of PCT application having application number PCT/US2019/020748, filed on Mar. 5, 2019 which application-claims priority to, and the benefit of, U.S. provisional application entitled "Dynamic Flow Phantom for In Vitro Cardiac Intervention Pre-Procedure Planning and Testing Using Patient Specific 3D Printed Anatomical Models" having Ser. No. 62/640,272, filed on Mar. 8, 2018, which is hereby incorporated by reference in its entirety.

BACKGROUND

Heart disease is the leading cause of death for both men and women in the United States. In fact, about 610,000 people die from heart disease every year, accounting for one in every four deaths. During the past 50 years, the landscape for heart disease has been changed by pharmacological advancements and device innovation for the management of coronary disease. Since acute myocardial infarctions (AMIs) are no longer terminal events, in-hospital mortality has been reduced by 10% and more individuals are surviving incident and subsequent heart attacks. However, after each myocardial insult, some patients develop chronic heart failure. As a result, the demand for interventional cardiology has increased. Clinicians are required to have experience with cutting edge technologies, such as 3D patient anatomical models, to plan cardiac surgical procedures and manage long-term patient healthcare with chronic heart failure and other cardiovascular interventions. Traditionally, the solutions to be implemented during the surgical procedures are planned mentally by the surgeon based on the imaging and models provided.

SUMMARY

Aspects of the present disclosure are related to a dynamic flow apparatus for cardiovascular diagnosis and pre-procedure analysis of individual patients.

In one aspect, among others, a dynamic flow apparatus, comprises an enclosed container, a three-dimensional (3D) cardiac model disposed within the enclosed container and being unique to a particular individual, one or more tubes coupled to one or more corresponding openings of the 3D cardiac model, a pump coupled to the one or more tubes and being configured to generate a pulsatile flow of fluid through the 3D cardiac model, and a beating apparatus configured to cause the 3D cardiac model to mimic a heartbeat.

In various aspects, the dynamic flow apparatus comprises a filling material disposed within the enclosed container, the filling material encapsulating the 3D cardiac model. In various aspects, the beating apparatus further comprises a pneumatic air source and a bladder, the bladder surrounding the 3D cardiac model. In various aspects, the beating apparatus further comprises a fixture pressed against the 3D cardiac model, the fixture being configured to rotate, thereby causing movement of the 3D cardiac model. In various aspects, the dynamic flow apparatus comprises one or more sensors being configured to measure environmental conditions of the 3D cardiac model. In various aspects, the environmental conditions comprise at least one of pressure, temperature, or hemodynamics. In various aspects, the dynamic flow apparatus comprises a miniaturized imaging device disposed within the 3D cardiac model. In various aspects, the miniaturized imaging device comprises an ultrasound device. In various aspects, the 3D cardiac model is printed via a 3D printing device based at least in part on imaging data obtained from the particular individual. In various aspects, the dynamic flow apparatus comprises a controller coupled to the pump, the controller being configured to control the pump. In various aspects, the 3D cardiac model comprises a deformable and elastic material. In various aspects, the deformable and elastic material is at least one of ultrasound or MRI compatible.

In another aspect, among others, a method comprises positioning a three-dimensional (3D) cardiac model within a dynamic flow apparatus, the 3D cardiac model being unique to an individual, causing the 3D cardiac model to mimic an operation of an actual heart of the individual by pumping a fluid through the 3D cardiac model and causing the 3D cardiac model to periodically expand and contrast, obtaining data associated with an operation of the 3D cardiac model, determining a condition associated with the operation of the 3D cardiac model based at least in part on the data, and determining a solution to the condition, the solution to be implemented on the actual heart of the individual during a surgical procedure.

In various aspects, the method further comprises obtaining imaging data from the individual and printing the 3D cardiac model on a 3D printing device using the imaging data obtained from the individual. In various aspects, the dynamic flow apparatus comprises an enclosed chamber, the 3D cardiac model being disposed within the enclosed chamber. In various aspects, the data comprises at least one of environmental or imaging data. In various aspects, the data comprises imaging data, and the imaging data is obtained from an imaging device disposed within the 3D cardiac model. In various aspects, the imaging device is disposed within the 3D cardiac model via at least one of a catheter or a probe. In various aspects, the data comprises environmental data, and the environmental data comprising at least one of pressure data, temperature data, or hemodynamic data. In various aspects, the method further comprise generating a modified 3D cardiac model implementing the solution to the condition, operating the dynamic flow apparatus using the modified 3D cardiac model, and verifying the solution according to data obtained from the modified 3D cardiac model.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims. In addition, all optional and preferred features and modifications of the described embodiments are usable in all aspects of the disclosure taught herein. Furthermore, the individual features of the dependent claims, as well as all optional and preferred features and modifications of the described embodiments are combinable and interchangeable with one another.

BRIEF DESCRIPTION OF THE DRAWINGS

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

DETAILED DESCRIPTION

Figure 1A:
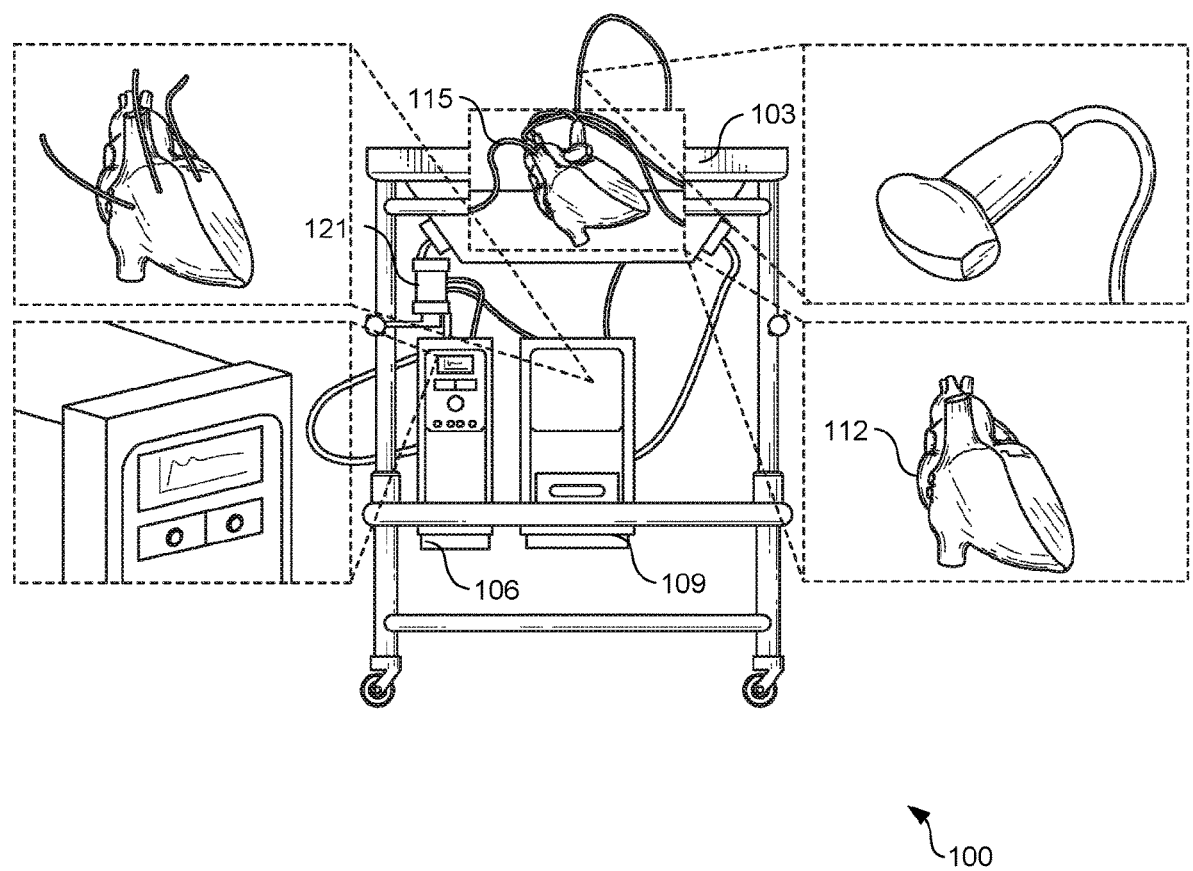
FIGS. 1A and 1B are example drawings of a dynamic flow apparatus, in accordance with various embodiments of the present disclosure.

Disclosed herein are various embodiments related to a dynamic flow apparatus for cardiovascular diagnosis and pre-procedure analysis of individual patients. The dynamic flow apparatus of the present disclosure is configured to apply a pulsatile flow through a three-dimensional (3D) cardiac model that is unique to a particular individual to test cardiac events. The dynamic flow apparatus can be used to evaluate a diagnosis for the particular patient, plan a procedure that is unique to the individual according to the individual's condition, and test the unique procedure to evaluate cardiac intervention prior to surgery. In some embodiments, the dynamic flow apparatus is further configured to cause the 3D cardiac model to expand and contrast in order to simulate the realistic physiology of a beating heart.

Three-dimensional (3D) printing is a widely used technique that builds life-like replicas of anatomical structures, such as the heart, to overcome and address the planning stages of these operative and procedural limitations. 3D printing is at the intersection of materials engineering, noninvasive diagnostic imaging, computer aided design, and structural heart intervention. The application of 3D printing has been increasingly utilized in medicine, with research supporting cardiology implementation. In fact, a recent systematic review has indicated that 3D printed models on medical imaging modalities can accurately replicate complex, anatomical features of the cardiovascular system, ultimately becoming a useful tool for surgical planning for cardiovascular disease and intervention methods. 3D printed patient-specific models are used by physicians to visualize or measure patient-specific anatomy in order to make an appropriate diagnosis or manage treatment recommendations.

3D printed anatomical models are useful tools for preoperative planning and orientation, as well as the simulation of actual procedures. 3D printed models have changed the overall healthcare landscape and the way that medicine is practiced for surgeons and physicians. Physicians have an opportunity to practice and study on exact replicas of patients' organs, such as the heart, leading to decreased procedure time and fewer complications. As a result, hospitals and healthcare providers are embracing 3D printing technology. 3D printed patient specific models can be used by physicians to visualize or measure patient specific anatomy to effectively help them make a better diagnosis or manage patient outcomes. The dynamic flow apparatus of the present disclosure can effectively model patient specific cardiovascular states (for example, normal vs. congenital heart disease).

The dynamic flow apparatus of the present disclosure can be used for pre-surgery, in vitro testing of cardiac interventions. The ultimate goals of the flow phantom and cardiac models of the present disclosure are to help diagnose complex cases and determine appropriate interventions, plan the procedure, and test the chosen intervention prior to being applied with the actual patient. This disclosed technology further overcomes single mode analysis limitations that do not accurately depict all the boundary conditions of an actual intervention (the disclosed technology is multi-modal in nature). One competitive advantage of the disclosed technology is that it allows physicians and surgeons a sophisticated method to acquire valuable information and make critical decisions regarding a chosen intervention prior to being implemented in an actual surgical procedure. The ability to see an actively beating model and the path of physiology in response to the heartbeat allows the physician to determine a solution prior to surgery. In some embodiments, a computational model of the heart using obtained imaging data can be used as an additional verification for the pre-treatment solution. In some embodiments, additional 3D cardiac models can be generated implementing the changes associated with the solution and can be tested using the dynamic flow apparatus for additional verification prior to surgery.

Figure 1B:
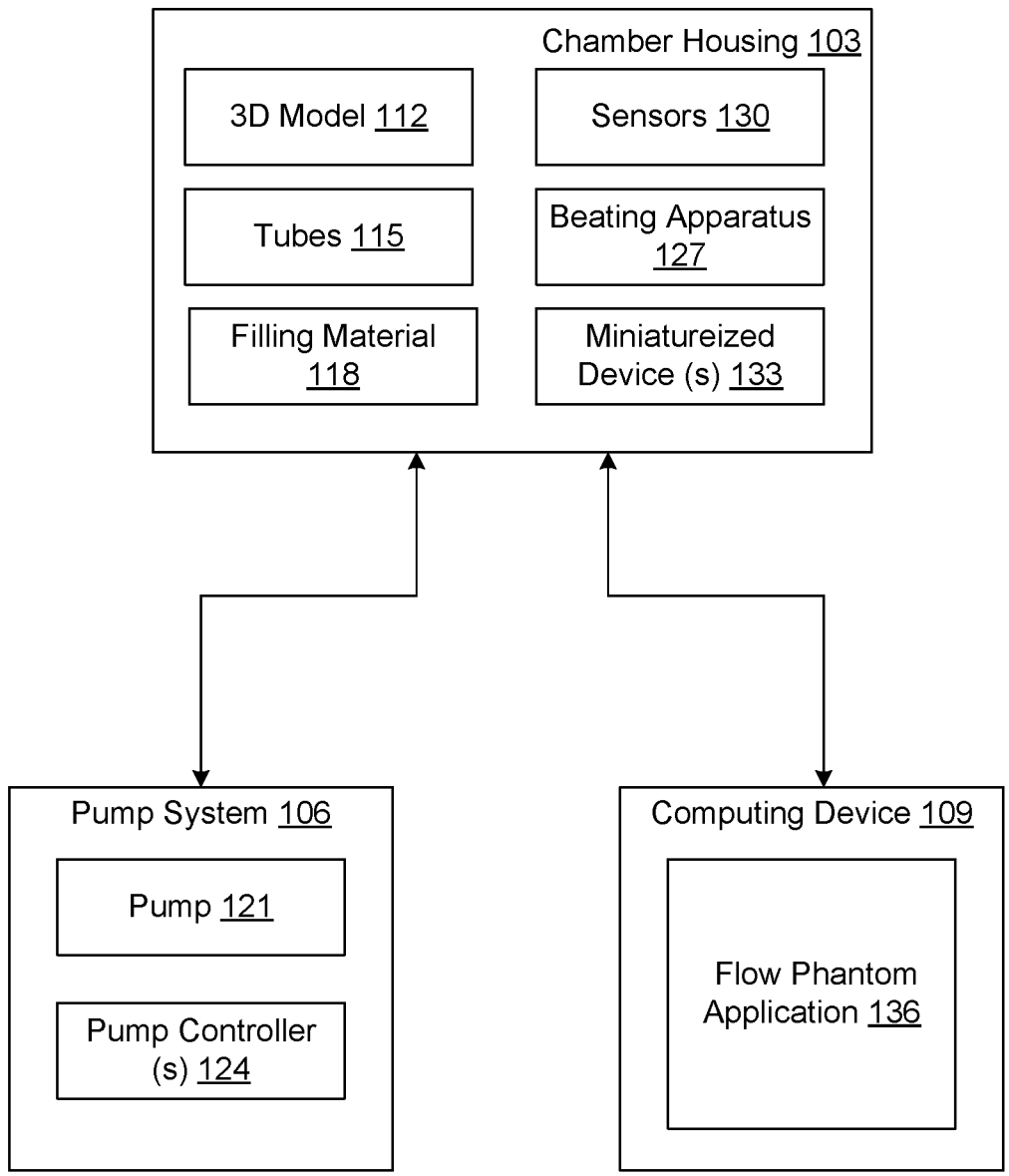

Turning now to FIGS. 1A and 1B, shown are example drawings of a dynamic flow apparatus 100 according to various embodiments of the present disclosure. In particular, FIG. 1A illustrates an example drawing of a dynamic flow apparatus 100 in an example operable configuration according to various embodiments. FIG. 1B illustrates an example block diagram illustrating the various components of the dynamic flow apparatus 100 according to various embodiments.

The dynamic flow apparatus 100 comprises an in vitro chamber housing 103, a pump system 106, and a computing device 109. A patient-specific 3D cardiac model 112 can be placed inside the chamber housing and can be coupled to the pump system 106 via one or more tubes 115. The 3D cardiac model 112 is unique to a particular patient and can be modeled using imaging techniques, such as, for example, CT scans, MRI scans, and/or any other type of imaging models, as can be appreciated. The 3D cardiac model 112 can be printed according to known 3D printing techniques. For example, the 3D cardiac model can be generated using stereolithography, fused deposition modeling, lost core molding, and/or other types of 3D printing techniques. In some embodiments, the 3D cardiac model 112 is opaque to allow for imaging into areas of interest (e.g., valve, chamber, mass, etc.). In other embodiments, the 3D cardiac model 112 is translucent.

The 3D cardiac model 112 can comprise an elastic and deformable material that allows the cardiac model to mimic the elasticity and mechanical properties of the soft tissue of a heart. For example, in some embodiments, the elastic and deformable material can comprise silicone. In other embodiments, the elastic and deformable material of the 3D cardiac model 112 can comprise an elastic material that is ultrasound and/or MRI compatible, such as, for example, Polyvinyl Alcohol (PVA) and hydrogel composites. By using a 3D cardiac model 112 that is unique to a particular patient, physicians can model a pre-procedure plan that is specific to the patient and the patient's unique condition.

The chamber housing 103 comprises an enclosed container that is configured to house the 3D cardiac model 112. The chamber housing 103 can be any shape and/or size as can be appreciated. In one non-limiting example, the chamber housing may comprise a geometric-shaped 3D structure (e.g., cuboid, cylinder, pentagon, etc.). In another non-limiting example, the chamber housing 103 can comprise a manikin-type structure that provides an environment that mimics that of an actual patient. According to various embodiments, the interior of the chamber housing 103 is filled with a filling material 118 (FIG. 1B) to encapsulate the 3D cardiac model 112 disposed within the chamber housing 103. The filling material 118 can comprise a hydrogel material, and/or any other type of material that can provide a physiological relevance as can be appreciated.

The dynamic flow apparatus 100 further comprises tubes 115 attached to openings of the 3D cardiac model 112 (e.g., arteries, valves, veins, etc.) that provide a path to the appropriate interior chambers of the heart. The tubes 115 are further coupled to the pump system 106. The tubes 115 and the pump system 106 are configured to provide fluid through the interior chambers of the 3D cardiac model 112 to simulate the operation of the heart as can be appreciated.

According to various embodiments, the pump system 106 comprises one or more pumps 121 controlled by one or more pump controllers 124. The one or more pump controllers 124 are configured control the fluid flow and/or pressure throughout the 3D cardiac model 112. In some embodiments, the pumps 121 comprise pulsatile pumps for simulating fluid flow through the cardiac model 112. The fluid comprises a fluid that mimics the properties of blood. For example, the fluid can have the scattering properties of blood for ultrasound analysis and imaging.

In various embodiments, the controllers 124 are integrated in a computing system comprising a processor and a memory. In some embodiments, the pump controllers 124 can be adjusted for a particular fluid flow or pressure as can be appreciated. The adjustment can be made using user input and/or learned models. According to various embodiments, the pump system 106 can comprises a display that can display pressure and/or flow data as can be appreciated.

According to various embodiments, the dynamic flow apparatus 100 can comprise a beating apparatus 127 that can cause the 3D cardiac model 112 to deform and mimic the manner in which a heart beats. By allowing the 3D cardiac model 112 to beat, a physician can analyze the physiology of the chambers of the 3D cardiac model 112 by observing the structure motion of the cardiac model and simulating blood moving in and out of the 3D cardiac model 112. The 3D cardiac model 112 can beat using pneumatic and/or mechanical methods as can be appreciated.

In one non-limiting example, using a pneumatic approach, the beating apparatus 127 can comprise a compressed air mechanism and a bladder positioned around the 3D cardiac model 112. Compressed air can be used in conjunction with the bladder to cause compressions and expansions of the 3D cardiac model 112. In another non-limiting example, a mechanical fixture can be coupled to the 3D cardiac model 112 within the chamber housing 103. For example, the mechanical fixture can be configured to press against the 3D cardiac model 112 and rotate to mimic the manner in which a heart pumps. In another non-limiting example, the beating apparatus 127 can comprise a pulsatile pump that can be used to create different beating events.

According to various embodiments, the type of beating apparatus 127 can be based at least in part on the desired application and image to be obtained. For example, a pneumatic approach can create a suction pressure that can allow a physician to analyze the suction of the chambers by creating a negative pressure. While CT and/or MRI images can be obtained using the pneumatic approach, ultrasound images would not be possible. When ultrasound images are desired, the mechanical approach can be implemented.

In various embodiments, the dynamic flow apparatus 100 comprises sensors 130 that can be used to measure environmental conditions such as, for example, pressure, temperature, hemodynamic differences, and/or other environmental conditions as can be appreciated. For example, the dynamic flow apparatus 100 can comprise transducers positioned up and down stream which can be used to measure pressure and determine a pressure difference. The sensor data can be used to gain a better understanding of the particular patient's anatomy and unique condition. The sensor data can further be used as a factor in determining a pre-treatment solution. In some embodiments, the dynamic flow apparatus 100 comprises one or more miniaturized devices 133 that can be disposed within the 3D cardiac model 112 via a probe, catheter, and/or other device as can be appreciated. The miniaturized devices 133 can comprise ultrasound devices and/or other types of imaging devices that can provide images to allow the individual to view the 3D cardiac model 112 from the inside out. According to various embodiments, the sensors 130 and/or the miniaturized devices 133 can be in data communication with the computing device 109. For example, the sensors 130 and/or miniaturized devices 133 can be in data communication with the computing device 109 via a wired connection and/or over wireless communication, as can be appreciated. Data collected by the sensors 130 and/or miniaturized devices 133 can be transmitted to the computing device 109 for analysis and display.

The computing device 109 can be representative of one or more computing devices. The computing device 109 can include a processor-based system, such as a computer system, that can include a desktop computer, a laptop computer, a personal digital assistant, a cellular telephone, a smartphone, a set-top box, a tablet computer system, or any other device with like capability. The computing device 109 can also be equipped with networking capability or networking interfaces, including a localized networking or communication capability, such as a near-field communication (NFC) capability, radio-frequency identification (RFID) read or write capability, or other localized communication capability.

The computing device 109 can include an operating system configured to execute various applications, such as the flow phantom application 136 and/or other applications. Some applications can render a user interface on a display, such as a liquid crystal display (LCD), touch-screen display, or other type of display device.

The flow phantom application 136 is configured to obtain data associated with the 3D cardiac model 112. According to various embodiments, the data can be obtained from the sensors 130, the miniaturized devices 133, and/or any other type of device as can be appreciated. The data can include imaging data, pressure data, environmental conditions data, and/or any other data as can be appreciated. In some embodiments, the data can be obtained from an ultrasound imaging probe interacting with the 3D cardiac model 112 within the enclosed chamber 103. For example, as a user moves the ultrasound imaging probe within the enclosed housing, data obtained from the probe can be sent to the flow phantom application 136 being executed on the computing device 109.

In some embodiments, the flow phantom application 136 can generate a user interface for displaying the data obtained for review by a user, such as, for example a physician. In some embodiments, the user can review the data and determine a condition associated with the 3D cardiac model 112 and/or the tested procedure with the 3D cardiac model 112. The user can further analyze the data to determine a solution for resolving the condition prior to performing the actual procedure on a patient. In other embodiments, the flow phantom application 136 can use learned data and/or other mathematical models to analyze the data and determine a condition and/or solution associated with the operation.

According to various embodiments of the present disclosure, the input parameters and hemodynamic monitoring can be used to model and optimize various interventions. For example, heart valve sizing can be tested using the 3D cardiac model 112. In this example, the heart valve sizing can be tested, iterated, and optimized, in-vitro, to provide the optimal therapeutic outcome.

Figure 2:
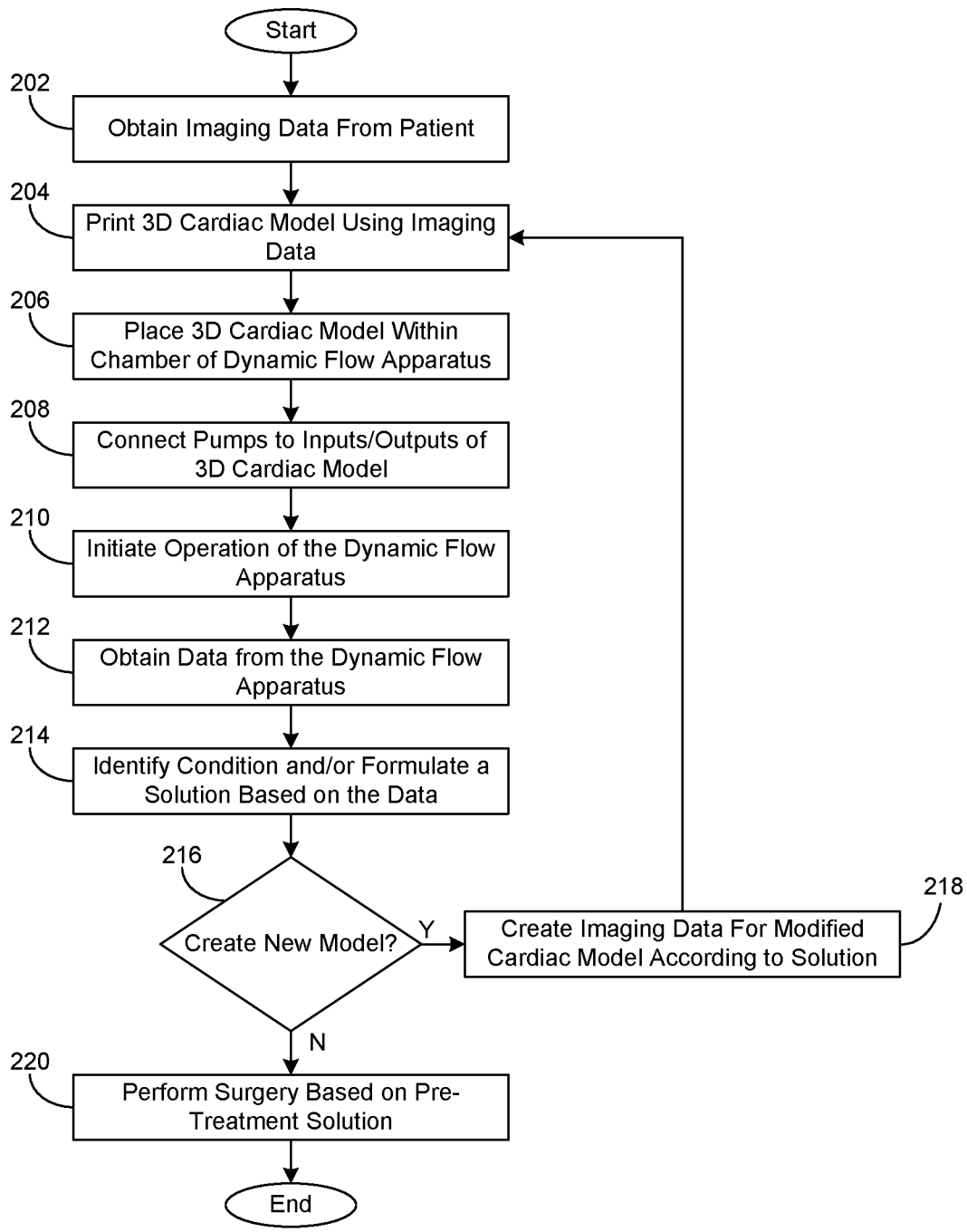
FIG. 2 is flowchart associated with the operation of the dynamic flow apparatus, in accordance with various embodiments of the present disclosure.

Turning now to FIG. 2, shown is a flowchart that provides one example of operation associated with the dynamic flow apparatus 100 according to various embodiments. It is understood that the flowchart of FIG. 2 provides merely an example of the many different types of functional arrangements that may be employed to implement the operation of the dynamic flow apparatus 100 as described herein. As an alternative, the flowchart of FIG. 2 may be viewed as depicting an example of elements of a method associated with dynamic flow apparatus 200 according to one or more embodiments.

Starting with numeral 202, imaging data specific to a patient is obtained via an MRI, a CT scan, and/or any other imaging device as can be appreciated. For example, imaging data associated with the patient's heart can be obtained and used to generate computational models and/or other models of the patient's heart as can be appreciated.

At numeral 204, the 3D cardiac model 112 that is unique to the patient can be printed using the captured imaging data and a typical 3D printer. For example, the 3D cardiac model can be generated using stereolithography, fused deposition modeling, lost core molding, and/or other types of 3D printing techniques. At numeral 206, the 3D cardiac model 112 is placed in the chamber housing 103 of a dynamic flow apparatus 100. At numeral 208, the openings of the 3D cardiac model 112 are connected to the various tubes 115 and pumps 121 that allow testing of the 3D cardiac model 112. For example, the tubes 115 are connected to the openings corresponding to the various valves, arteries, and/or veins of the 3D cardiac model 112 to allow for a pulsatile flow to be incorporated within the 3D cardiac model 112, thereby mimicking the operation of the patient's actual heart.

At numeral 210, operation of the dynamic flow apparatus 100 is initiated. The dynamic flow apparatus 100 comprises a pump system 106 including one or more controllers 124 that can be used to control the pumps 121 associated with the pulsatile flow running through the 3D cardiac model 112. In addition, the 3D cardiac model 112 can be configured to beat via the use of a beating apparatus 127. As such, the 3D cardiac model 112 can begin beat according to the beating method (e.g., mechanical, pneumatic, etc.) associated with the particular dynamic flow apparatus 100.

At numeral 212, data from the dynamic flow apparatus 100 can be obtained. The data can correspond to imaging data, pressure data, environmental conditions data, and/or any other data as can be appreciated. For example, the dynamic flow apparatus 100 can comprise sensors 130 disposed at various sections of the 3D cardiac model 112 that are configured to measure pressure differences associated with the inflow and outflow of the 3D cardiac model 112. In another non-limiting example, ultrasound data and/or other type of imaging data can be obtained to allow the physician a better understanding of the operation of the 3D cardiac model 112.

At numeral 214, a condition and/or a surgical solution can be identified and/or formulated according to the function and operation of the 3D cardiac model 112 within the dynamic flow apparatus 100. Based on the procedure of the 3D cardiac model 112 via the dynamic flow apparatus 100, a physician can gain a better understanding of the operation of the patient's specific heart and can visualize the pulsatile flow through the appropriate chambers and valves. In some embodiments, the 3D cardiac model 112 can be a model that has been modified according to the solution, and the physician can determine the effectiveness of the solution based on the data obtained during operation of the dynamic flow apparatus 100.

At numeral 216, it is determined whether a new model 112 is to be created based at least in part on the condition and/or solution identified based in part on the data obtained during the operation of the dynamic flow apparatus. For example, a physician can identify a solution to improve and/or correct a condition that is unique to a particular patient prior to a surgical procedure. In some embodiments, the physician can verify that results of the change by implementing an additional 3D cardiac model 112 that includes the change. If a new model 112 is to be created, the flowchart proceeds to numeral 218. Otherwise, the flowchart proceeds to numeral 220.

At numeral 218, imaging data is created for the modified 3D cardiac model 112. For example, the imaging data originally obtained to create the original 3D cardiac model 112 can be computationally modified to implement the proposed changes based on the identified solution. After the modified imaging data is created, the flowchart proceeds to numeral 204, and the modified 3D cardiac model is printed and ultimately tested in the dynamic flow apparatus 100. At numeral 220, the surgical procedure is performed on the patient according to the identified and/or verified solution that was determined using the dynamic flow apparatus 100.

A number of software components are stored in the memory and executable by a processor. In this respect, the term "executable" means a program file that is in a form that can ultimately be run by the processor. Examples of executable programs can be, for example, a compiled program that can be translated into machine code in a format that can be loaded into a random access portion of one or more of the memory devices and run by the processor, code that can be expressed in a format such as object code that is capable of being loaded into a random access portion of the one or more memory devices and executed by the processor, or code that can be interpreted by another executable program to generate instructions in a random access portion of the memory devices to be executed by the processor. An executable program can be stored in any portion or component of the memory devices including, for example, random access memory (RAM), read-only memory (ROM), hard drive, solid-state drive, USB flash drive, memory card, optical disc such as compact disc (CD) or digital versatile disc (DVD), floppy disk, magnetic tape or other memory components.

Memory can include both volatile and nonvolatile memory and data storage components. Also, a processor can represent multiple processors or multiple processor cores, and the one or more memory devices can represent multiple memories that operate in parallel processing circuits, respectively. Memory devices can also represent a combination of various types of storage devices, such as RAM, mass storage devices, flash memory, or hard disk storage. In such a case, a local interface can be an appropriate network that facilitates communication between any two of the multiple processors or between any processor and any of the memory devices. The local interface can include additional systems designed to coordinate this communication, including, for example, performing load balancing. The processor can be of electrical or of some other available construction.

Although the controllers 124, the flow phantom application 136, and other various services and functions described can be embodied in software or code executed by general purpose hardware as discussed above, as an alternative, the same can also be embodied in dedicated hardware or a combination of software/general purpose hardware and dedicated hardware. If embodied in dedicated hardware, each can be implemented as a circuit or state machine that employs any one of or a combination of a number of technologies. These technologies can include discrete logic circuits having logic gates for implementing various logic functions upon an application of one or more data signals, application specific integrated circuits (ASICs) having appropriate logic gates, field-programmable gate arrays (FPGAs), or other components.

The flowcharts show an example of the functionality and operation of an implementation of portions of components described. If embodied in software, each block can represent a module, segment, or portion of code that can include program instructions to implement the specified logical function(s). The program instructions can be embodied in the form of source code that can include human-readable statements written in a programming language or machine code that can include numerical instructions recognizable by a suitable execution system such as a processor in a computer system or other system. The machine code can be converted from the source code. If embodied in hardware, each block can represent a circuit or a number of interconnected circuits to implement the specified logical function(s).

Although the flowcharts show a specific order of execution, it is understood that the order of execution can differ from that which is depicted. For example, the order of execution of two or more blocks can be scrambled relative to the order shown. Also, two or more blocks shown in succession can be executed concurrently or with partial concurrence. Further, one or more of the blocks shown in the drawings can be skipped or omitted.

Also, any logic or application described that includes software or code can be embodied in any non-transitory computer-readable medium for use by or in connection with an instruction execution system such as a processor in a computer system or other system. In this sense, the logic can include, for example, statements including instructions and declarations that can be fetched from the computer-readable medium and executed by the instruction execution system. In the context of the present disclosure, a "computer-readable medium" can be any medium that can contain, store, or maintain the logic or application described for use by or in connection with the instruction execution system.

The computer-readable medium can include any one of many physical media, such as magnetic, optical, or semiconductor media. More specific examples of a suitable computer-readable medium include solid-state drives or flash memory. Further, any logic or application described can be implemented and structured in a variety of ways. For example, one or more applications can be implemented as modules or components of a single application. Further, one or more applications described can be executed in shared or separate computing devices or a combination thereof. For example, a plurality of the applications described can execute in the same computing device, or in multiple computing devices.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include traditional rounding according to significant figures of numerical values. In addition, the phrase "about 'x' to 'y'" includes "about 'x' to about 'y'".

The invention claimed is:

1. A dynamic flow apparatus, comprising:
an enclosed container;
a three-dimensional (3D) cardiac model disposed within the enclosed container, the 3D cardiac model being unique to a particular individual;
one or more tubes coupled to one or more corresponding openings of the 3D cardiac model;
a pump coupled to the one or more tubes, the pump being configured to generate a pulsatile flow of fluid through the 3D cardiac model; and
a beating apparatus configured to cause the 3D cardiac model to mimic a heartbeat, wherein the beating apparatus further comprises a pneumatic air source and a bladder, the bladder surrounding the 3D cardiac model.

2. The dynamic flow apparatus of claim 1, further comprising a filling material disposed within the enclosed container, the filling material encapsulating the 3D cardiac model.

3. The dynamic flow apparatus of claim 1, further comprising one or more sensors being configured to measure environmental conditions of the 3D cardiac model.

4. The dynamic flow apparatus of claim 3, wherein the environmental conditions comprise at least one of pressure, temperature, or hemodynamics.

5. The dynamic flow apparatus of claim 1, further comprising a miniaturized imaging device disposed within the 3D cardiac model.

6. The dynamic flow apparatus of claim 5, wherein the miniaturized imaging device comprises an ultrasound device.

7. The dynamic flow apparatus of claim 1, wherein the 3D cardiac model is printed via a 3D printing device based at least in part on imaging data obtained from the particular individual.

8. The dynamic flow apparatus of claim 1, further comprising a controller coupled to the pump, the controller being configured to control the pump.

9. The dynamic flow apparatus of claim 1, wherein the 3D cardiac model comprises a deformable and elastic material.

10. The dynamic flow apparatus of claim 9, wherein the deformable and elastic material is at least one of ultrasound or MRI compatible.

11. A method, comprising:
positioning a three-dimensional (3D) cardiac model within a dynamic flow apparatus, the 3D cardiac model being unique to an individual;
causing the 3D cardiac model to mimic an operation of an actual heart of the individual by:
pumping a fluid through the 3D cardiac model using a pump of the dynamic flow apparatus; and
causing the 3D cardiac model to periodically expand and contract using a beating apparatus of the dynamic flow apparatus, wherein the beating apparatus comprises one of:
a pneumatic air source and a bladder, the bladder surrounding the 3D cardiac model to cause the 3D cardiac model to periodically expand and contract; or
a fixture pressed against the 3D cardiac model, the fixture being configured to rotate, thereby causing the 3D cardiac model to periodically expand and contract;
obtaining data associated with an operation of the 3D cardiac model;
determining a condition associated with the operation of the 3D cardiac model based at least in part on the data; and
determining a solution to the condition, the solution to be implemented on the actual heart of the individual during a surgical procedure.

12. The method of claim 11, further comprising:
obtaining imaging data from the individual; and
printing the 3D cardiac model on a 3D printing device using the imaging data obtained from the individual.

13. The method of claim 11, wherein the dynamic flow apparatus comprises an enclosed chamber, the 3D cardiac model being disposed within the enclosed chamber.

14. The method of claim 11, wherein the data comprises at least one of environmental or imaging data.

15. The method of claim 14, wherein data comprises imaging data, and the imaging data is obtained from an imaging device disposed within the 3D cardiac model.

16. The method of claim 15, wherein the imaging device is disposed within the 3D cardiac model via at least one of a catheter or a probe.

17. The method of claim 14, wherein the data comprises environmental data, and the environmental data comprising at least one of pressure data, temperature data, or hemodynamic data.

18. The method of claim 11, further comprising:
generating a modified 3D cardiac model implementing the solution to the condition;
operating the dynamic flow apparatus using the modified 3D cardiac model; and
verifying the solution according to data obtained from the modified 3D cardiac model.

19. A dynamic flow apparatus, comprising:
an enclosed container;
a three-dimensional (3D) cardiac model disposed within the enclosed container, the 3D cardiac model being unique to a particular individual;
one or more tubes coupled to one or more corresponding openings of the 3D cardiac model;
a pump coupled to the one or more tubes, the pump being configured to generate a pulsatile flow of fluid through the 3D cardiac model; and
a beating apparatus configured to cause the 3D cardiac model to mimic a heartbeat, wherein the beating apparatus further comprises a fixture pressed against the 3D cardiac model, the fixture being configured to rotate, thereby causing movement of the 3D cardiac model.

* * * * *